(12) United States Patent
Bradshaw

(10) Patent No.: US 11,199,597 B2
(45) Date of Patent: Dec. 14, 2021

(54) COIL SYSTEMS FOR MAGNETIC RESONANCE IMAGING

(71) Applicant: INVIVO CORPORATION, Andover, MA (US)

(72) Inventor: Kenneth Bradshaw, Bear, DE (US)

(73) Assignee: Invivo Corporation, Andover, MA (US)

( * ) Notice: Subject to any disclaimer, the term of this patent is extended or adjusted under 35 U.S.C. 154(b) by 1733 days.

(21) Appl. No.: 14/774,992

(22) PCT Filed: Mar. 10, 2014

(86) PCT No.: PCT/US2014/022446
§ 371 (c)(1),
(2) Date: Sep. 11, 2015

(87) PCT Pub. No.: WO2014/159192
PCT Pub. Date: Oct. 2, 2014

(65) Prior Publication Data
US 2016/0022142 A1 Jan. 28, 2016

Related U.S. Application Data

(60) Provisional application No. 61/784,787, filed on Mar. 14, 2013.

(51) Int. Cl.
*G01R 33/36* (2006.01)
*A61B 5/055* (2006.01)
(Continued)

(52) U.S. Cl.
CPC ............ *G01R 33/365* (2013.01); *A61B 5/004* (2013.01); *A61B 5/055* (2013.01); *A61B 5/4312* (2013.01);
(Continued)

(58) Field of Classification Search
CPC ....... A61B 5/004; A61B 5/055; A61B 5/0555; A61B 5/4312; A61B 5/0091;
(Continued)

(56) References Cited

U.S. PATENT DOCUMENTS 6,441,615 B1  8/2002  Fujita et al.
6,930,481 B2  8/2005  Okamoto et al.
(Continued)

*Primary Examiner* — James M Kish

(57) ABSTRACT

A RF coil compression system for use with an MRI system configured to image a patient's breast is disclosed. In one embodiment, the compression system comprises a first compression plate comprising a first plurality of RF coil elements, which is positioned in a plane oriented orthogonal to a direction of the main magnetic field and the first RF coil elements having a reception sensitivity to a B1 field and is orthogonal to a main magnetic field of the MRI system. The compresses system may further comprise a second compression plate, configured to be positioned opposing the first compression plate and orthogonal to the superior-inferior direction, the second compression plate comprising a second plurality of RF coil elements, the second RF coil elements having a reception sensitivity to a B1 field oriented in a direction substantially orthogonal to the first direction and to the main magnetic field of the MRI system.

20 Claims, 7 Drawing Sheets

(51) Int. Cl.
*A61B 5/00* (2006.01)
*G01R 33/34* (2006.01)
*G01R 33/3415* (2006.01)

(52) U.S. Cl.
CPC .......... *A61B 5/708* (2013.01); *G01R 33/3415* (2013.01); *G01R 33/34084* (2013.01); *G01R 33/34069* (2013.01)

(58) Field of Classification Search
CPC .......... G01R 33/34084; G01R 33/3415; G01R 33/365; G01R 33/34; G01R 33/34007; G01R 33/34023
See application file for complete search history.

(56) References Cited

U.S. PATENT DOCUMENTS

| | | | |
|---|---|---|---|
| 7,772,842 B2* | 8/2010 | Gao | G01R 33/307 324/307 |
| 7,970,452 B2 | 6/2011 | Piron | |
| 2001/0039378 A1 | 11/2001 | Lampman | |
| 2003/0109782 A1 | 6/2003 | Su | |
| 2003/0208121 A1 | 11/2003 | Baltschun et al. | |
| 2005/0228267 A1* | 10/2005 | Bulkes | A61B 6/0414 600/415 |
| 2007/0016003 A1* | 1/2007 | Piron | A61B 5/415 600/415 |
| 2007/0250047 A1* | 10/2007 | Harter | A61B 5/0555 606/1 |
| 2008/0071164 A1* | 3/2008 | Pogue | A61B 5/0091 600/411 |
| 2008/0077005 A1* | 3/2008 | Piron | A61B 5/0555 600/411 |
| 2008/0306377 A1 | 12/2008 | Piron | |
| 2009/0082663 A1 | 3/2009 | Guan | |
| 2011/0034796 A1 | 2/2011 | Ma et al. | |

* cited by examiner

COIL SYSTEMS FOR MAGNETIC RESONANCE IMAGING

CROSS-REFERENCE TO PRIOR APPLICATIONS

This application is the U.S. National Phase application under 35 U.S.C. § 371 of International Application No. PCT/US2014/022446, filed on Mar. 10, 2014, which claims the benefit of U.S. Patent Application No. 61/784,787, filed on Mar. 14, 2013. These applications are hereby incorporated by reference herein.

BACKGROUND

Field of the Invention

The present invention relates to magnetic resonance imaging (MRI), in particular to a coil system for imaging of breast tissue.

Background of the Art

Breast cancer is one of the leading causes of death in women. As a result, early detection is important, and screening of all women is encouraged. Magnetic resonance imaging (MRI) is commonly used to provide non-invasive methods to visualize any abnormalities in the patient's breast tissue.

MRI detects the nuclear magnetic resonance signals given off by protons in the presence of a strong magnetic field after excitation by a radio frequency signal. The nuclear magnetic resonance signals are detected using one or more antenna(e), RF coils or "coils." The term "coil" may be used to refer to the antenna itself and its housing or support structure. Thus "coil" may refer to a structure that contains one or more coils. "Coil element(s)" may be used to refer to the electrical part of the device, the radiofrequency coil or antennae.

Sensitivity of a coil to magnetic resonance signals decreases rapidly with increasing distance between the coils and the volume of interest. It is therefore desirable to place coils in close proximity to the breast. The size of the local coils is kept small to allow them to be easily fit to the patient on the MRI patient table and to enable imaging of only the imaging volume of interest, since imaging regions that are not required adds noise to the acquired signal unnecessarily. Coils local to the anatomy of interest tend to have a higher signal-to-noise ratio (SNR) than larger coils such as a "body coil" which is useful for obtaining large survey scans of the patient. Coils can be operated individually, as multiple coils in a phased array, circularly polarized or in quadrature mode. Combining signals from multiple coils can yield improvements in SNR.

SUMMARY

Patient support structures designed for imaging of a patient's breast comprise one or more imaging coils which are removable and replaceable with regard to the patient support structure. Typically, the coils used in these patient support structures are positioned in the Z-Y plane in order to image the breast in a sagittal frame. Sagittal slices taken using these coils can be reconfigured in coronal and axial directions to provide different perspectives. In these systems, sagittal slices are chosen because of the orientation of the coils. The coils and supporting mechanism previously used with the patient support systems are typically designed to compress the breast in the left to right (or mediolateral) direction.

Increasingly, however, there is a desire to view the breast bilaterally without reconfiguring the data from the sagittal plane to the coronal and axial plane. This requires that the data be obtained axially. With the typical left to right compression, the number of axial slices obtained by the MRI system may increase, thus increasing overall imaging time. Because the imaging compressing systems used in the MRI imaging procedure are typically uncomfortable for the patient, the increase in the overall imaging time can cause the patient additional discomfort. In addition, with the previously described left to right compression, the axial slices can decrease in sensitivity and result in images of lower quality.

Accordingly, aspects and embodiments described herein comprise coils and supporting mechanism designed to be disposed in the X-Y plane and to compress the breast in the cranio-caudal (superior-inferior) direction. Stabilizing the breast decreases the number of slices required to obtain a complete image of the entire breast. Positioning the coils in the X-Y plane and compressing the breast in the superior-inferior direction decreases the number of axial slices that need to be obtained by the MRI system, thus faster throughput without sacrificing imaging of the relevant tissue and reducing the amount of discomfort experienced by the patient. It is appreciated that with aspects and embodiments of the disclosure, the compression of the breast is not as excessive as it is in Mammography which compresses the breast to decrease the thickness of the tissue to be imaged. The compression or stabilization described herein with reference to the compression plates and compression system will be slight and thus improving patient comfort.

The use of the coil configurations described herein for cranio-caudal compression would not be typically considered by a person having ordinary skill in the art, because the use of coils in the frame in the cranio-caudal orientation would be considered counter-intuitive. Placing typical coils, such as the circular surface coils, in cranio-caudal orientation would not result in detection of the magnetic resonance signals, because the flux lines would be in the same direction as the main field. For typical lateral compression, using butterfly or microstrip coils is not as attractive because these types of coils are not as sensitive as circular surface coils for use in cranio-caudal compression. Other coil systems use butterfly coils only in lateral compression and only as part of single loops so as to decouple coils on opposite sides of the breast.

However, the coil systems described herein, according to various embodiments, use butterfly coils, or butterfly coils combined with stripline coils, for breast imaging in the cranio-caudal direction. By using the butterfly coil configuration described herein, in the cranio-caudal configuration, the magnetic field going in one loop of the butterfly coil and out the other loop of the butterfly coil can create flux lines linking the two fields in-between the two loops which the magnetic flux lines are parallel to the coils. Therefore, the butterfly coil would have reception sensitivity that is parallel to the surface of the butterfly coil and orthogonal to the main magnetic field, thereby detecting the magnetic resonance signals.

According to one aspect, a RF coil compression system for use with an MRI system having a main magnetic field configured to image a patient's breast is disclosed. In one embodiment, the RF coil compression system comprises a first compression plate configured to be adjacent to the patient's breast comprising a first plurality of RF coil elements, the first compression plate positioned in a plane oriented orthogonal to a direction of the main magnetic field and also orthogonal to a superior-inferior direction, the first RF coil elements having a reception sensitivity to a B1 field substantially oriented in a first direction throughout the breast wherein the first direction is configured to be orthogonal to the main magnetic field of the MRI system. The RF coil compression system also comprises a second compression plate, configured to be positioned opposing the first compression plate and on an other side of the breast and parallel to the first compression plate and also orthogonal to the superior-inferior direction, the second compression plate comprising a second plurality of RF coil elements, the second RF coil elements having a reception sensitivity to a B1 field oriented in a direction substantially orthogonal to the first direction and to the main magnetic field of the MRI system throughout the patient's breast.

According to various embodiments, the compression system can include any one or more of the following: the first and the second compression plates may be configured to compress the patient's breast in the superior-inferior direction; the first and the second compression plates may be integrated into a patient support structure; the first compression plate is moveably coupled to the second compression plate to enable the first and the second compression plates to be moved together along the superior-inferior direction for immobilization of the patient's breast there between; the first plurality of RF coil elements and the second plurality of RF coil elements each comprise a first butterfly RF coil element, disposed adjacent to a second butterfly RF coil element, wherein the first butterfly RF coil element is configured to overlap the second butterfly RF coil element along a length of the first and the second butterfly RF coil elements;

the first and the second plurality of RF coil elements may each comprise a third butterfly RF coil element, disposed adjacent to a fourth butterfly RF coil element, wherein the third butterfly RF coil element is configured to overlap the fourth butterfly RF coil element along a length of the third and the fourth butterfly RF coil elements; the first butterfly RF coil element overlaps with the third butterfly RF coil element along a width of the first and the third butterfly RF coil elements;

the second butterfly RF coil element overlaps with the fourth butterfly RF coil element along a width of the second and the fourth butterfly RF coil elements; the first butterfly RF coil element, the second butterfly RF coil element, the third butterfly RF coil element and the fourth butterfly RF coil element may overlap in a central area of each butterfly RF coil element respectively;

the first plurality of RF coil elements and the second plurality of RF coil elements each further comprise a third butterfly RF coil element disposed adjacent the second butterfly RF coil element, and a fourth butterfly RF coil element disposed adjacent to the third butterfly RF coil element; the third butterfly RF coil element is configured to overlap the second butterfly RF coil element along a length of the second and the third butterfly RF coil elements, and the fourth butterfly RF coil element is configured to overlap the third butterfly RF coil element along a length of the second and the third butterfly RF coil elements;

a first stripline RF coil element disposed along the length of a middle of the first butterfly RF coil element and a second stripline RF coil element disposed along the length of a middle of the second butterfly RF coil element; a third stripline RF coil element disposed along the length of a middle of the third butterfly RF coil element and a fourth stripline RF coil element disposed along the length of a middle of the fourth butterfly RF coil element;

the first and the second compression plates are contoured to fit partially around the patient's breast; the first compression plate is moveably coupled to the second compression plate to enable the first and the second compression plates to be moved together along the superior-inferior direction for immobilization of the patient's breast there between;

the first plurality of RF coil elements and the second plurality of RF coil elements each comprise a first butterfly RF coil element disposed adjacent to a second butterfly RF coil element, wherein the first butterfly RF coil element and the second butterfly RF coil element are contoured to the shape of the first and second compression plates; the first butterfly RF coil element is configured to overlap the second butterfly RF coil element along a length of the first and the second butterfly RF coil elements.

Still other aspects, embodiments, features and advantages of these exemplary aspects and embodiments, are discussed in detail below. Any feature, advantage, implementation, embodiment, or example may be combined or form a part of any aspect or any embodiments in any manner consistent with at least one of the principles disclosed herein, and references to "an embodiment," "some embodiments," "an alternate embodiment," "various embodiments," "one embodiment," "example," "feature," "advantage," "implementation" or the like are not necessarily mutually exclusive and are intended to indicate that a particular feature, embodiment, structure, or characteristic described may be included in at least one aspect. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure. In the figures.

DETAILED DESCRIPTION

Figure 1:
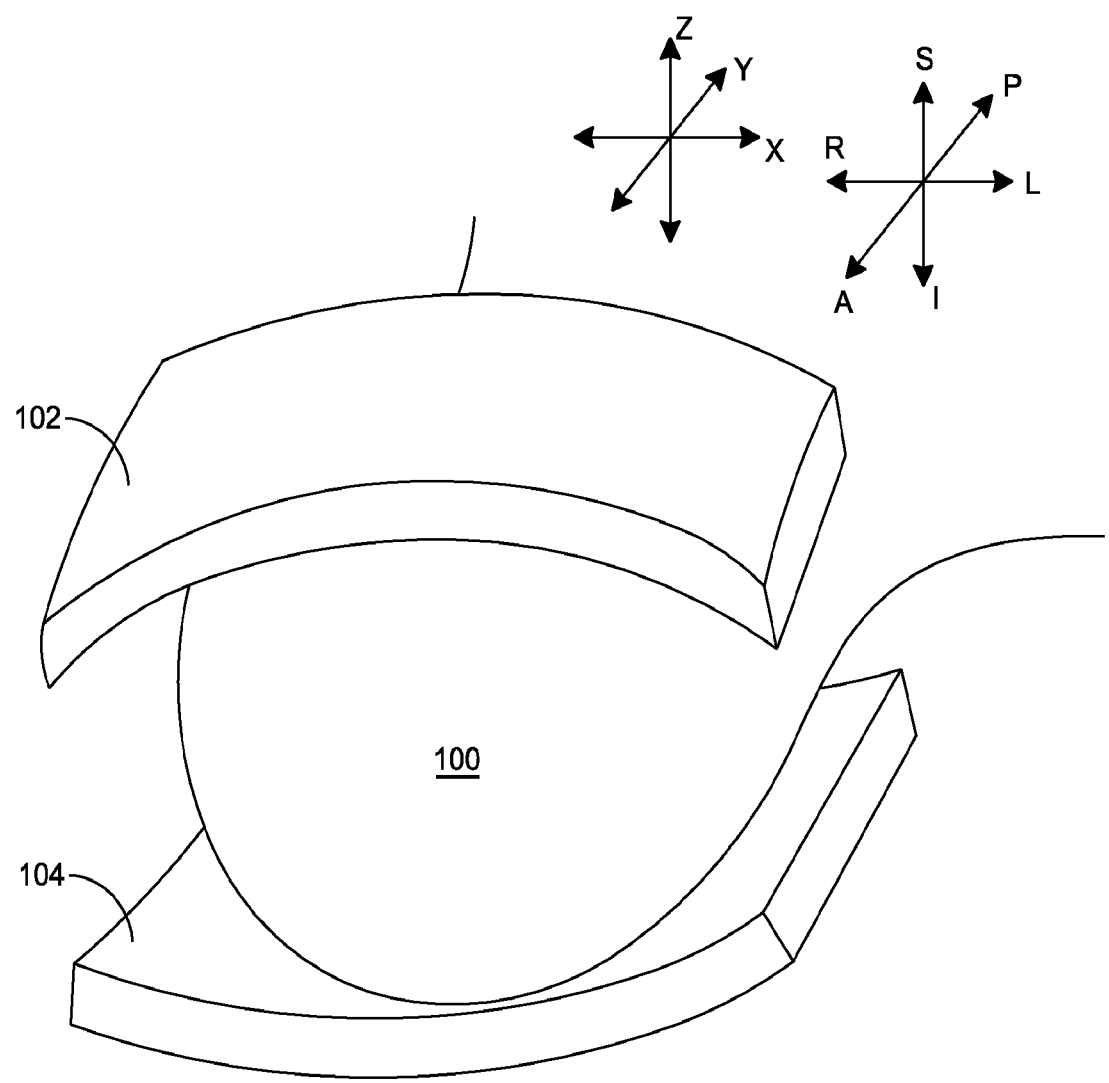
FIG. 1 is a diagram of compression plates, including an embedded coil system, compressing a breast of a patient, according to one embodiment.

Aspects and embodiments of this disclosure are directed to system of coils used in the cranio-caudal (or superior/inferior) compression of the breast. Unlike previously disclosed systems, which disclose compression in the left and right lateral directions, cranio-caudal compression of the breast (in the superior/inferior directions) allows the imaging system to image the breast to obtain axial slices without reconfiguring the acquired data for the axial perspectives. If other perspectives are required, they may be reconfigured from the axial data. Aspects and embodiments are directed to coil configurations including a combination overlapping coils disposed in the X-Y plane and having reception sensitivity to a B1 field which is substantially oriented in a direction that is orthogonal to direction of the main B0 magnetic field from the MRI. The combination overlapping coils, according to the embodiments described, allows for acceleration of data acquisition decreasing the time of the scan. In addition, the coil and compression systems described herein decrease the number of slices needed to cover the entire breast. As a result, the coil systems and compression systems compressing the breast in the superior-inferior directions decrease the total imaging time and increase patient comfort.

As referenced herein, in imaging applications, the Z-direction also coincides with the direction of the B0 magnetic field produced by the MR imager and also coincides with the axial plane which separates the head (superior(S) or cranio direction) from the feet (inferior (I) or caudal direction). The B1 labels the magnetic field having two rotating vectors, in a plane that is orthogonal to B0.

The antennae, or RF coils used with MRI systems may include transmit and/or receive coils of various designs. The RF antenna may include basic RF components including the RF coil conductor, broken into multiple segments with distributed capacitors. At one of the junctions a passive blocking circuit may be included, with an additional active blocking circuit, which may be activated by a bias signal from the MRI system. Various additional circuits and components are desirable and can be included as part of the RF coil systems.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiment.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

FIG. 1 illustrates one embodiment of coil compression plates 102 and 104, configured to compress the breast 100 in the cranio-caudal (superior-inferior) directions. Unlike the previously disclosed coil systems and the compression plates, the coil compression plates 102 and 104 are disposed in the X-Y plane and move in the superior-inferior directions in relation to the breast. As shown, the coil compression plates 102 and 104 may be curved to provide a better fit to the breast shape. In other embodiments, coil compression plates may be flat and straight.

As noted above, in the examples described, the coil compression plate 102, and the associated coil system is configured to move in the inferior (I) directions, while the coil compression plate 104 and the associated coil system is configured to move in the superior (S) directions. The coil compression plates 102 and 104 are configured to move closer and farther apart from each one to compress and release the breast 100. Once the coil compression plates 102 and 104 are moved in the desired position, the plates 102 and 104 may be locked in relation to each other.

In some examples, the size and the curvature of the coil compression plates may be different to allow for breasts of different sizes. In one example, the coil compression plates 102 and 104 are configured to be movable with respect to each other, allowing breasts of different sizes to fit into the coil compression plates. The plates can be moved concurrently or one of the plates can be kept stationary while the other plate is moved with respect to the other. In addition, the compression plates may be connected to each other and to other structural components including connecting elements, main medial and lateral supports. Further, the compression plates may be incorporated into a patient support structure, as described below and with reference to Published U.S. Pat. No. 7,970,452, filed on Aug. 28, 2006, titled "Open Architecture Imaging Apparatus and Coil System for Magnetic Resonance Imaging," which is incorporated herein by reference in its entirety and is hereinafter referred to the '452 patent. Although only one set of coil compression plates is shown, it is appreciated that an additional set of coil compression plates can be used for bilateral imaging.

Figure 2A:
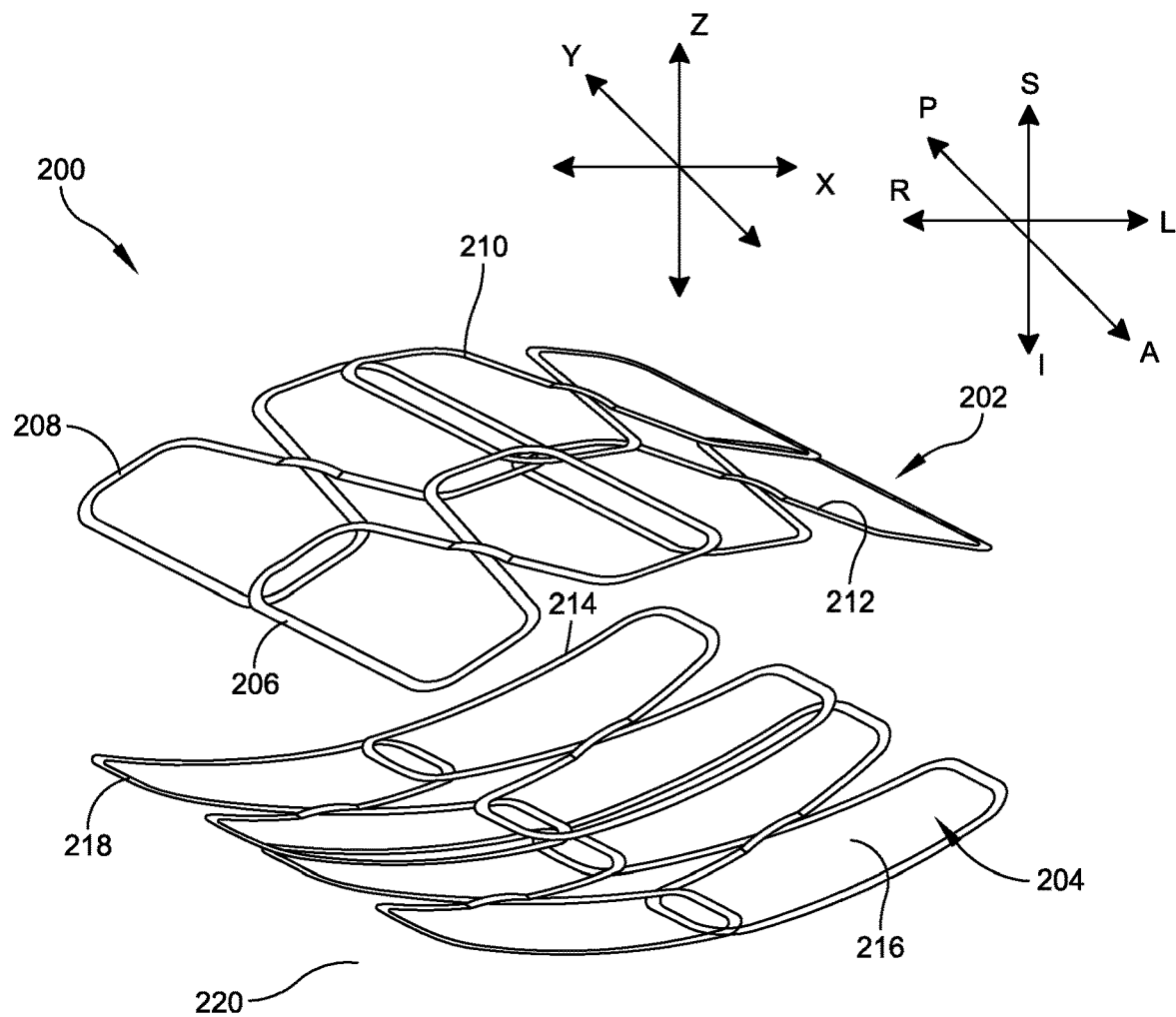
FIGS. 2A-2B are diagrams of coil systems embedded in the compression plates, according to one embodiment.
Figure 2B:
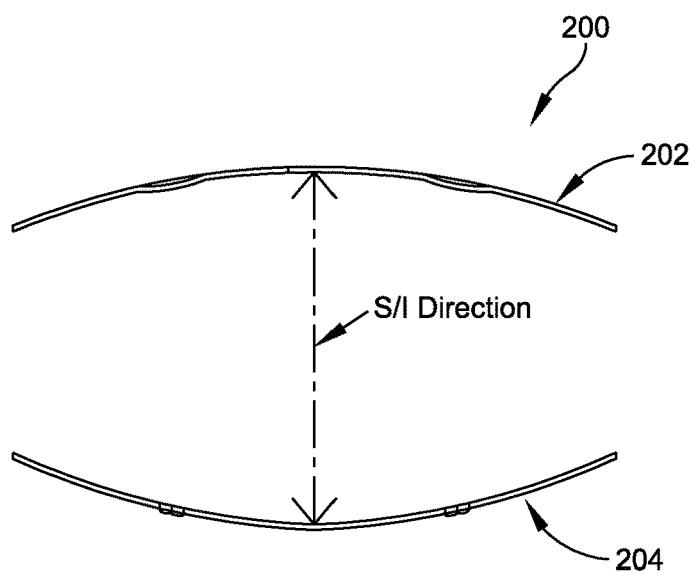
Figure 2C:
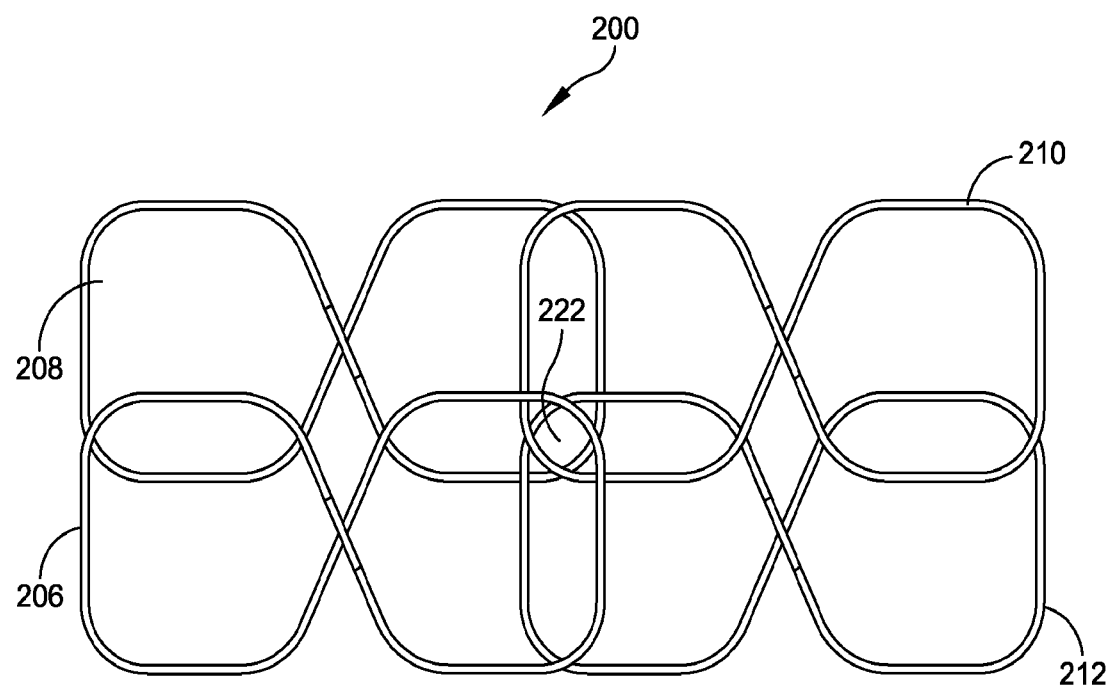
FIG. 2C is a diagram of a coil system in a different orientation, according to one embodiment.

One or more coil systems, having different geometries, may be embedded into the coil compression plates. FIGS. 2A-2C illustrate one example of a combination of overlapping coils 202 and 204 included in a coil system 200, which may be embedded in the coil compression plates of FIG. 1. Although only one set of coil systems is shown, it is appreciated that an additional set of coil systems can be used for bilateral imaging.

The coils 202 and 204 may be curved to fit the curvature of the coil compression plates 102 and 104, as shown in FIGS. 2A and 2B. The combination overlapping coil structure 200 has the advantage of providing acceleration in both anterior-posterior and the left-right lateral directions. The combination overlapping coil structures can also be used in straight compression plates.

Other geometries may be embedded in the compression plates, which are described further in reference to FIGS. 3A-4B. It is appreciated that coil coupling may occur not only within the plane of the array but also through breast tissue. Therefore, the orientation of the coils opposing and parallel to each other should be placed such that their sensitivity fields are orthogonal to each other to minimize coupling. With the Z-direction coinciding with the direction of the B0 magnetic field produced by the MR imager, the sensitivity of the coils in the Z-direction is due to the detection of spins in the X-Y plane. Typically, stimulated magnetic fields are not be detected by surface coils in X-Y plane. However, the coil geometries disclosed herein and shown in FIGS. 2A-4B are configured to detect the stimulated magnetic fields.

In the examples described, the coils 202 have reception sensitivity to a B1 field, substantially oriented in a direction that is orthogonal to Z-direction, which coincides with the main magnetic field B0 of the MRI system. The coils 202 and 204 have reception sensitivity in a direction that is orthogonal to the B1 field.

The superior combination of overlapping coils 202 includes the butterfly coils 208-212, while the inferior combination of overlapping coils 204 includes the butterfly coils 214-220. Each of butterfly coils comprises circular loop coil that is twisted in the middle of the loop to create a "figure 8" shape having two loops. Therefore, the resultant butterfly coil includes a first loop, a twist in the middle, and a second loop symmetrical to the first loop disposed opposite the first loop.

FIG. 2C illustrates the superior combination of overlapping coil 202 in more detail. The butterfly coils 208 and 206 are disposed adjacent to each other with edges of the first and second parts of the coils overlapping each other along the length of the coils in the sagittal direction. Similarly, the butterfly coils 210 and 212 are disposed adjacent to each other and the edges of the first and second parts overlap each other along the length of the coils in the sagittal direction. In turn, edges of the first and second parts of the butterfly coil 206 overlap with the edges of the first and second parts of the butterfly coil 212 along the width of the coils in the coronal direction. Similarly, the butterfly coil 208 overlaps with the butterfly coil 210 in the coronal direction. All of the coils 208-212 include a central overlap area 222 at the center of the superior combination coil 202.

In the configuration shown, the magnetic field going in one loop of the butterfly coil and out the other loop of the butterfly coil can create flux lines linking the two fields in-between the two loops which the magnetic flux lines are parallel to the coils. Therefore, the butterfly coil configuration shown described here would have reception sensitivity that is parallel to the surface of the butterfly coil and orthogonal to the main magnetic field, thereby detecting the magnetic resonance signals.

The coupling between the superior combination coil 202 and the inferior combination coil 204 is minimized by using orthogonal configurations of similar coil shapes. Having substantially orthogonal field lines helps to reduce inductive coupling between coils. In this way coils can be densely packed to cover the patient's breast without interfering with one another, giving rise to optimal SNR and allowing for parallel imaging methods. The dimensions of the individual butterfly coils 214-220 in the combination coil 204 may be changed to fit the sizes and shapes of the compression plates. Other butterfly coils in the configuration may be similarly sized.

Part of the challenge associated with using multiple coils for imaging is the fact that the fields of individual coils may interact, resulting in coil-to-coil coupling, where these interactions serve to reduce the coil quality factor. The butterfly coils may be similarly dimensioned and symmetrical with respect to each other. The symmetrical nature and the overlap of the butterfly coils can reduce inductive coupling. It is appreciated that the amount of overlap may be determined by the dimensions of the compression coil plates and the amount of coupling between the coils. In some examples, the amount of overlap is 10% such that their additional field contributions cancel resulting in no coupling. It is appreciated that other amounts of overlap can be used.

In some embodiments, coil coupling may occur between non-nearest neighbors in which the field cancellations are complicated significantly. In these cases, coupling can be reduced through the addition of capacitors, inductors or additional circuits between coils which experience some amount of coupling. Low-impedance preamplifiers may be added to the coil system which can reduce the effects of coil coupling.

According to various embodiments, the coil systems include overlapping coil systems of multiple geometries which are disposed in coil compression plates, disposed in the superior-inferior directions or the X-Y plane. The coil configurations shown in FIGS. 3A-4B include different configurations of butterfly coils combined with stripline coils. With the coil geometries disclosed, it is a matter of choosing the appropriate orientation and combination to provide the best sensitivity and provide optimum parallel imaging. It is appreciated that there may be several coil structures and geometries that can be configured to be used in the superior-inferior (cranio-caudal) directions and provide the necessary amount of decoupling and sensitivity needed for the application. It is appreciated that all of these configurations or combinations of configurations can be used as needed.

Stripline or microstrip coils can be combined with butterfly coils to achieve a type of quadrature reception. FIGS. 3A-4B illustrate some examples of overlapping combination coils including a combination of stripline coils and butterfly coils. Stripline coils detect signals whose orientation is orthogonal to the direction of the stripline. It is appreciated that the max sensitivity comes with vertical surface coils (orthogonal to the surface of the coil) and coils with horizontal fields (parallel to the surface of the coil) are only about 70% of the vertical coils.

Figure 3A:
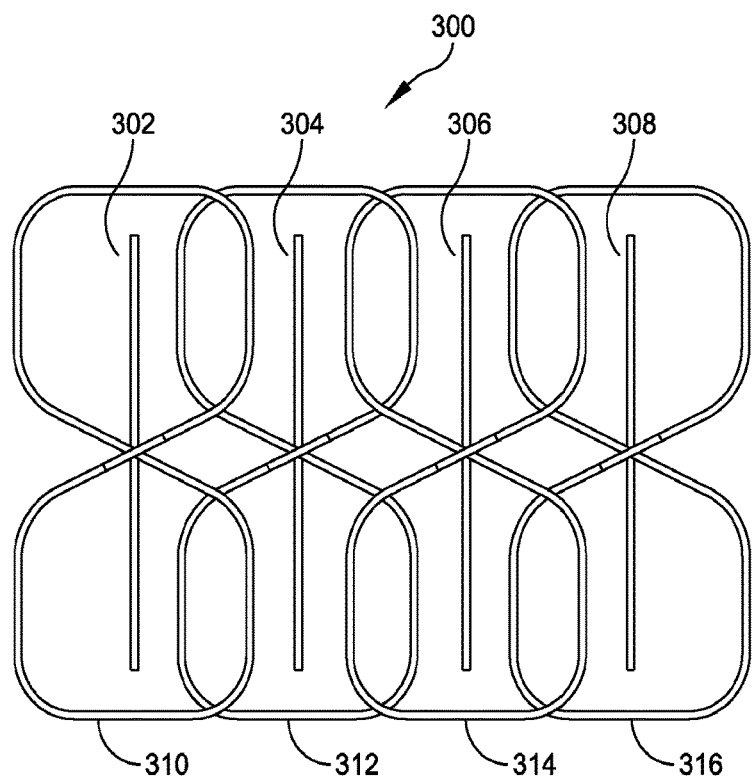
FIGS. 3A-3B are diagrams of coil systems embedded in the compression plates, according to another embodiment.

FIG. 3A illustrates one example of a combination butterfly and stripline coil system 300 that includes four stripline coils 302, 304, 306 and 308 and four butterfly coils 310, 312, 314 and 316. The butterfly coils are disposed along the same direction, with edges of each of the butterfly coils overlapping along the length of the length of the coil. Each of the coils overlaps by a predetermined amount with an adjacent butterfly coil. In turn, the stripline coils are disposed along the length of the butterfly coil through the center of each butterfly coil.

In the embodiment shown in FIG. 3A, edges of the butterfly coil 310 overlap with edges of the butterfly coil 312 on one side. Edges of butterfly coil 312 overlap with edges of butterfly coil 314 on the other side of butterfly coil 312. The edges on other side of the butterfly coil 314 overlap with edges of the butterfly coil 316. The stripline coil 302 is disposed through the center of the butterfly coil 310 and the stripline coil 304 is disposed through the center of the butterfly coil 312. The stripline coil 306 is disposed through the center of the butterfly 314 and the stripline coil 308 is disposed through the center of the butterfly coil 316.

Figure 3B:
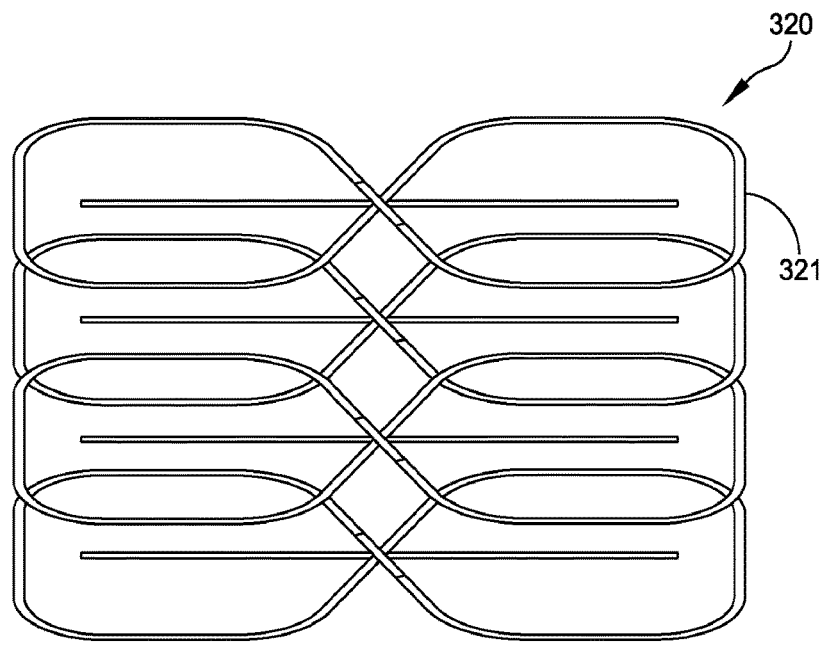

The coil system 300 can be embedded in a coil compression plate and disposed in the X-Y plane. FIG. 3B illustrates a corresponding coil system 320 having the configuration of coils similar to coil system 300 which may be disposed below the coil system 300 in the X-Y plane. The coupling between the superior coil system 300 and the inferior coil system 320 is minimized by positioning the inferior coil system 320 orthogonal with relation to the superior coil system 300. The dimensions of the individual butterfly and stripline coils 302-316 and the butterfly and stripline coils in the coil system 320 may be changed to fit the orientation of the compression plates. For example, the width dimension of the butterfly coil 321 may correspond to the length dimension of the butterfly coils in the coil system 320. Other butterfly coils in the configuration may be similarly sized.

Figure 4A:
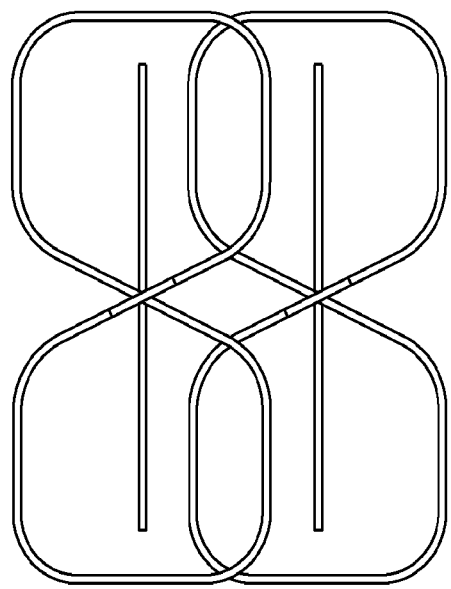
FIGS. 4A-4B are diagrams of coil systems embedded in the compression plates, according to another embodiment.
Figure 4B:
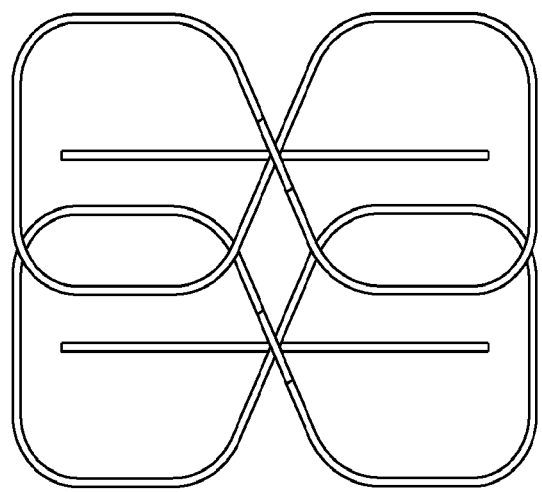

FIGS. 4A and 4B show coils systems having geometries similar to FIGS. 3A and 3B and may be used in smaller compression plates. In these embodiments, the coil systems include two overlapping butterfly coils and two stripline coils disposed at the center of the butterfly coils. As discussed above, one of the coil systems may be disposed orthogonal to the other coil system to provide decoupling.

Further consideration with coil systems is their ability to operate in a parallel imaging mode. In these modes of operation, imaging techniques such as SMASH, SENSE, PILS or GRAPPA, require coils to be imaging independent volumes. Based on the sensitivity profiles of these coils operating independently, a reconstruction algorithm can be implemented that enables reconstruction of a full image volume in a fraction of the conventional image acquisition time. Coils should image independent volumes for optimal parallel imaging, and therefore decoupling strategies that employ overlapping of coils are non optimal.

Signals from individual coil elements can be combined in phased-array, quadrature or circularly polarized arrangements. The preferred embodiments are presented with interchangeable coil plates containing coils in phased array and quadrature arrangements in various geometries and various orientations. The arrangement of the coils on these plates contributes to the overall sensitivity profile and field-of-view of the combined coil array. Therefore the size, position, phase variation and orientation of the coils is considered to optimize the overall sensitivity, field uniformity, field coverage, coil coupling and parallel imaging characteristics of the entire coil arrangement.

Figure 5:
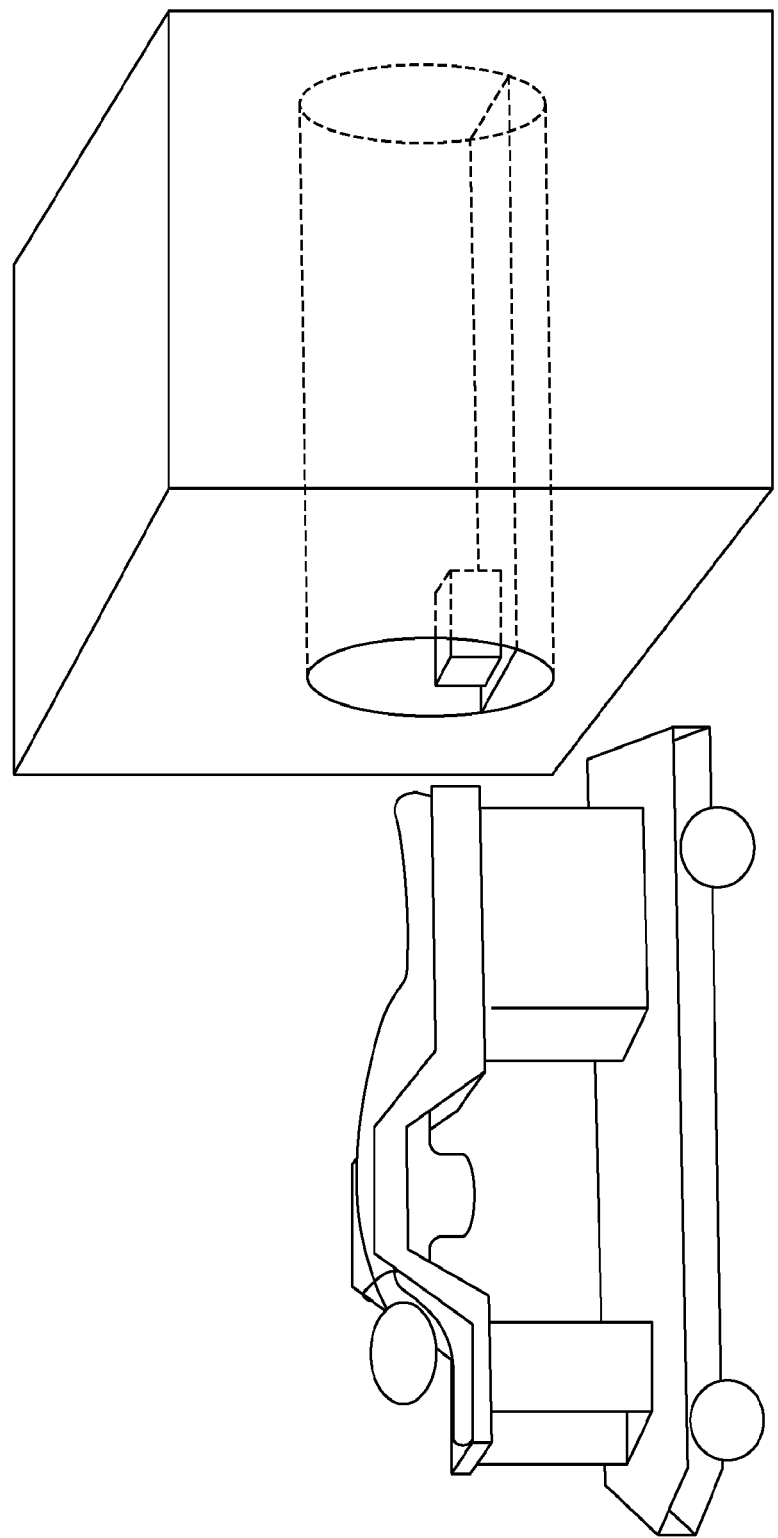
FIG. 5 is diagram of a patient support structure and an MRI imager, according to one embodiment.

The compression plates described above may be part of a patient support system. FIG. 5 illustrates one example of a patient support system in which the compression plates together with the RF coils can be disposed. The patient support structure comprises a dedicated transport stretcher and a tabletop patient support system which is placed on top of the transport stretcher. The patient support system may be a specialized tabletop support system configured to image a specific anatomy, such as the breast. The patient support system may include secondary support structures including one or more compression plates and imaging coils which are removable and replaceable with regard to the patient support structure. The patient support structures, according to various embodiments, are described in the '452 Patent.

As shown in FIG. 5, the patient lies prone in preparation for MRI breast imaging on a main patient support structure that sits on top of the transport stretcher. The primary patient support structure, together with secondary support structures and one or more compression plates and imaging coils, are inserted into the bore of the imager.

The patient support structures include an aperture in which the compression plates and the imaging coils are incorporated. The coils systems and compression plates described in the '452 patent are positioned in the Z-Y plane, while the coils systems, while the compression plates of this disclosure are disposed in the X-Y plain. The patient support structure can include secondary support structures that can be attached to the primary support structure to optimally position the patient's tissues for imaging or interventional applications. The coil systems described herein can be used as part of a variable geometry system that provides the ability to vary the coil's proximity to the breast. Reducing the distance of the coil to the breast, resulting in better signal-to-noise (SNR). Other breast coils being marketed usually have constrained volumes but no variability in that volume and are at a disadvantage when the breast does not fit the shape of the coil array.

Figure 6A:
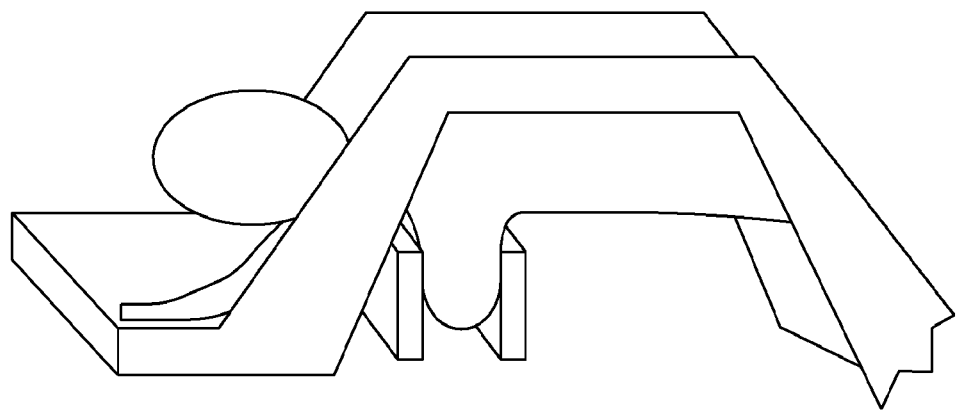
FIGS. 6A-6B are diagrams of a patient support structure and variable compression plates, according to one embodiment.
Figure 6B:
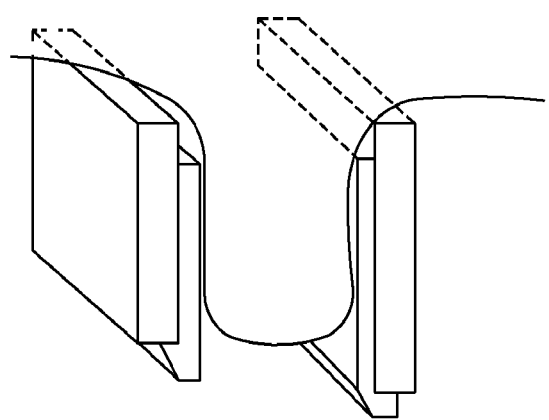

FIGS. 6A-6B illustrate one example of patient support system configured with the compression plates of the present disclosure. In at least one example, the coil compression plates may be part of a compression system, such as the compression system disclosed in the '452 patent. The compression system may include one or more additional or separate compression plates, such as anterior or posterior compression plates. In one example, the coil compression plates may be movably coupled together by one or more connecting elements, or other parts of the compression system such as elements part of the compression frame.

In some embodiments, the coil systems may be attached to or built directly into the coil compression plates and can be integrated into the coil system through any combination of a variety of means including: embedding (non separable) coils in the support structure; embedding coils in non-separable, but movable structures; separable RF coils in coil housings attached to the compression frames; separable RF coils in coil housings attached directly to the support structure; separable secondary support structures containing RF coils.

These coil compression plates can be connected to the main support structure both mechanically and electrically through a single locking/fixation means. The embedded coils in case can be directly connected to an MRI connector by way of the traditional means of electrical connection. Separable coils may be connected to the MRI via a connection panel or port provided within the support structure which is then attached to the MRI connection by way of electrical cables (or other such means). The coils that are attached to the moveable elements of the system such as the compression plates, the secondary infrastructure or embedded within the compression plates have the advantage of being placed very close to the anatomy resulting in high signal acquisition.

In other embodiments, the coil compression plates may provide mountings to which removable coil systems may be attached. The mountings, in some examples, may provide both mechanical connections to the overall compression system and, simultaneously signal connectivity to the MRI system, such that the act of connecting the coil element or elements to the movable compression plate also connects that coil's signals to the MRI system.

As noted above, the coil compression plates can be used in both unilateral and bilateral imaging applications. In unilateral breast imaging applications, a single breast of interest is immobilized and compressed between two coil plates which can be adjusted in superior/inferior directions and locked in place, while the other breast is compressed against the chest wall by a breast support. The ability to move these coil plates close to the breast significantly improves coil reception. In bilateral breast imaging application, arrays of multiple coils can be used. The bilateral imaging system includes a means of selecting subsets of coils to collect only MR signals from the selected volume of interest such as the patient's breast. In the case of bilateral contrast-enhanced breast imaging, it is desired to obtain individual breast volumes independently. Therefore a means of selecting a subset of coils during image acquisition of one breast, and another subset of coils for another breast is preferable.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only.

What is claimed is:

1. A system comprising:
   a structure which is configured to be inserted into a magnetic resonance imaging (MRI) system, wherein the structure comprises an aperture configured to receive a patient's breast;
   a first compression plate arranged adjacent to the aperture and at a first side of the aperture, wherein the first compression plate comprises a first plurality of radio frequency coil elements; and
   a second compression plate arranged adjacent to the aperture and at a second side of the aperture which is opposite the first side, wherein the second compression plate comprises a second plurality of radio frequency coil elements;
   wherein the first plurality of radio frequency coil elements and the second plurality of radio frequency coil elements each comprise a first butterfly radio frequency coil and a second butterfly radio frequency coil;
   wherein, when the structure is inserted into the MRI system and said patient's breast is received through said aperture, then the first compression plate and the first plurality of radio frequency coil elements are positioned in a plane oriented orthogonal to a direction of a main magnetic field of the MRI system and also orthogonal to a superior-inferior direction of the patient, wherein the first plurality of radio frequency coil elements have a reception sensitivity to a first B1 field which is substantially oriented in a first direction throughout the breast, wherein the first direction is orthogonal to the main magnetic field of the magnetic resonance imaging system, wherein the second plurality of radio frequency coil elements are positioned in a second plane oriented orthogonal to the direction of the main magnetic field and also orthogonal to the superior-inferior direction of the patient, and have a reception sensitivity to a second B1 field which is oriented in a second direction which is substantially orthogonal to the first direction and to the main magnetic field of the MRI system throughout the patient's breast.

2. The system of claim 1,
   wherein the first and the second compression plates are configured to compress the patient's breast in the superior-inferior direction; and/or wherein the first and the second compression plates are contoured to fit partially around the patient's breast.

3. The system of claim 1,
   wherein the first and the second compression plates are integrated into a structure.

4. The system of claim 1,
   wherein the first compression plate is moveably coupled to the second compression plate to enable the first and the second compression plates to be moved together along the superior-inferior direction for immobilization of the patient's breast there between.

5. The system of claim 1,
   wherein the first butterfly radio frequency coil of the first plurality of radio frequency coil elements is disposed adjacent to the second butterfly radio frequency coil of the first plurality of radio frequency coil elements, and the first butterfly coil of the second plurality of radio frequency coil elements is deposed adjacent to the second butterfly coil of the second plurality of radio frequency coil elements,
   wherein the first butterfly radio frequency coil of the first plurality of radio frequency coil elements overlaps the second butterfly radio frequency coil of the first plurality of radio frequency coil elements along a length of the first butterfly radio frequency coil and the second butterfly radio frequency coil of the first plurality of radio frequency coil elements, and the first butterfly coil of the second plurality of radio frequency coil elements overlaps the second butterfly radio frequency coil of the second plurality of radio frequency coil elements along a length of the first butterfly radio frequency coil and the second butterfly radio frequency coil of the second plurality of radio frequency coil elements.

6. The system of claim 5,
   wherein the first plurality of radio frequency coil elements further comprises a third butterfly radio frequency coil and a fourth butterfly radio frequency coil,
   wherein the third butterfly radio frequency coil is disposed adjacent to the fourth butterfly radio frequency coil,
   wherein the third butterfly radio frequency coil is configured to overlap the fourth butterfly radio frequency coil along a length of the third butterfly radio frequency coil and the fourth butterfly radio frequency coil.

7. The system of claim 6,
   wherein the first butterfly radio frequency coil of the first plurality of radio frequency coil elements overlaps with the third butterfly radio frequency coil of the first plurality of radio frequency coil elements along a width of the first butterfly radio frequency coil and the third butterfly radio frequency coil.

8. The system of claim 6, wherein the second butterfly radio frequency coil overlaps with the fourth butterfly radio frequency coil along a width of the second butterfly radio frequency coil and the fourth butterfly radio frequency coil.

9. The system of claim 8,
   wherein the first butterfly radio frequency coil, the second butterfly radio frequency coil, the third butterfly radio frequency coil and the fourth butterfly radio frequency coil overlap in a central area of each butterfly radio frequency coil.

10. The system of claim 6, further comprising a first stripline radio frequency coil element disposed along the length of a middle of the first butterfly radio frequency coil and a second stripline radio frequency coil element disposed along the length of a middle of the second butterfly radio frequency coil.

11. The system of claim 10, further comprising a third stripline radio frequency coil element disposed along the length of a middle of the third butterfly radio frequency coil and a fourth stripline radio frequency coil disposed along the length of a middle of the fourth butterfly radio frequency coil.

12. The system of claim 5,
   wherein the first butterfly radio frequency coil and the second butterfly radio frequency coil are contoured to the shape of the first compression plate and the second compression plate.

13. The system of claim 1, wherein the first butterfly radio frequency coil and second butterfly radio frequency coil of the first plurality of coils of the first compression plate are each oriented in a first coil orientation direction and the first butterfly radio frequency coil and second butterfly radio frequency coil of the second plurality of coils of the second compression plate are each oriented in a second coil orientation direction, and wherein the first coil orientation direction is orthogonal to the second coil orientation direction.

14. A method comprising:
positioning a first compression plate, which includes a first plurality of radio frequency coil elements, adjacent to a first side of a patient's breast, wherein positioning the first compression plate includes positioning the first compression plate and the first plurality of radio frequency coil elements in a plane oriented orthogonal to a direction of a main magnetic field of magnetic resonance imaging system and also orthogonal to a superior-inferior direction of the patient, wherein the first radio frequency coil elements have a reception sensitivity to a first B1 field which is substantially oriented in a first direction throughout the breast, wherein the first direction is orthogonal to the main magnetic field of the magnetic resonance imaging system; and
positioning a second compression plate opposing the first compression plate and on a second side of the patient's breast and parallel to the first compression plate and also orthogonal to the superior-inferior direction, wherein the second compression plate having includes a second plurality of radio frequency coil elements, wherein the second plurality of radio frequency coil elements are positioned in a second plane oriented orthogonal to the direction of the main magnetic field and also orthogonal to the superior-inferior direction of the patient, and have a reception sensitivity to a second B1 field which is oriented in a second direction which is substantially orthogonal to the first direction and to the main magnetic field of the magnetic resonance imaging system throughout the patient's breast,
wherein the first plurality if radio frequency coil elements and the second plurality of radio frequency coil elements each comprise a first butterfly radio frequency coil and a second butterfly radio frequency coil.

15. The method of claim 14,
wherein the first compression plate and the second compression plate are configured to compress the patient's breast in the superior-inferior direction; and
wherein the first and the second compression plates are contoured to fit partially around the patient's breast.

16. The method of claim 14,
wherein the first compression plate is moveably coupled to the second compression plate to enable the first and the second compression plates to be moved together along the superior-inferior direction for immobilization of the patient's breast there between.

17. The method of claim 15,
wherein the first butterfly radio frequency coil of the first plurality of radio frequency coil elements is disposed adjacent to the second butterfly radio frequency coil of the first plurality of radio frequency coil elements, and the first butterfly coil of the second plurality of radio frequency coil elements is disposed adjacent to the second butterfly coil of the second plurality of radio frequency coil elements,
wherein the first butterfly radio frequency coil of the first plurality of radio frequency coil elements overlaps the second butterfly radio frequency coil of the first plurality of radio frequency coil elements along a length of the first plurality of radio frequency coil elements, and the first butterfly coil of the second plurality of radio frequency coil elements overlaps the second butterfly radio frequency coil of the second plurality of radio frequency coil elements along a length of the first butterfly radio frequency coil and the second butterfly radio frequency coil of the second plurality of radio frequency coil elements.

18. The method of claim 17,
wherein the first plurality of radio frequency coil elements comprise a third butterfly radio frequency coil and a fourth butterfly radio frequency coil,
wherein the third butterfly radio frequency coil is disposed adjacent to the fourth butterfly radio frequency coil, wherein the third butterfly radio frequency coil is configured to overlap the fourth butterfly radio frequency coil along a length of the third butterfly radio frequency coil and the fourth butterfly radio frequency coil.

19. The method of claim 18, wherein the first butterfly radio frequency coil of the first plurality of radio frequency coil elements overlaps with the third butterfly radio frequency coil of the first plurality of radio frequency coil elements along a width of the first butterfly radio frequency coil and the third butterfly radio frequency coil.

20. The method of claim 14, wherein the first butterfly radio frequency coil and second butterfly radio frequency coil of the first plurality of coils of the first compression plate are each oriented in a first coil orientation direction and the first butterfly radio frequency coil and second butterfly radio frequency coil of the second plurality of coils of the second compression plate are each oriented in a second coil orientation direction, and wherein the first coil orientation direction is orthogonal to the second coil orientation direction.

* * * * *